(12) United States Patent
Emons et al.

(10) Patent No.: US 6,775,350 B2
(45) Date of Patent: Aug. 10, 2004

(54) METHOD OF EXAMINING A WAFER OF SEMICONDUCTOR MATERIAL BY MEANS OF X-RAYS

(75) Inventors: Catharina Huberta Henrica Emons, Nijmegen (NL); Henricus Godefridus Rafael Maas, Eindhoven (NL); Theodorus Martinus Michielsen, Eindhoven (NL); Ronald Dekker, Eindhoven (NL); Antonius Johannes Janssen, Nijmegen (NL); Ingrid Annemarie Rink, Nijmegen (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 15 days.

(21) Appl. No.: 10/242,924

(22) Filed: Sep. 13, 2002

(65) Prior Publication Data

US 2003/0053590 A1 Mar. 20, 2003

(30) Foreign Application Priority Data

Sep. 18, 2001 (EP) .............................. 01203526

(51) Int. Cl.⁷ .............................................. G01N 23/20
(52) U.S. Cl. .............................. 378/74; 378/71; 378/73
(58) Field of Search .................... 378/44–50, 70–90; 438/14, 16, 459, 476

(56) References Cited

U.S. PATENT DOCUMENTS

| | | | |
|---|---|---|---|
| 3,609,356 A | * | 9/1971 | Schwuttke et al. ........... 378/74 |
| 3,716,712 A | * | 2/1973 | Piwczyk ...................... 378/74 |
| 3,944,823 A | * | 3/1976 | Chikawa ...................... 378/74 |
| 4,928,294 A | | 5/1990 | Beard, Jr. et al. ............. 378/74 |
| 4,959,848 A | | 9/1990 | Parobek ....................... 378/46 |
| 5,007,071 A | * | 4/1991 | Nakano et al. ............... 378/74 |
| 5,077,767 A | * | 12/1991 | Gaukroger .................... 378/73 |
| 5,754,620 A | * | 5/1998 | Hossain et al. ............... 378/45 |
| 6,226,349 B1 | * | 5/2001 | Schuster et al. .............. 378/84 |
| 6,376,267 B1 | * | 4/2002 | Noack et al. ................. 438/16 |
| 6,385,289 B1 | * | 5/2002 | Kikuchi ....................... 378/79 |
| 2003/0108152 A1 | * | 6/2003 | Bowen et al. ................ 378/74 |

FOREIGN PATENT DOCUMENTS

WO WO9616443 5/1996 ......... H01L/23/528

* cited by examiner

*Primary Examiner*—Edward J. Glick
*Assistant Examiner*—Allen C. Ho
(74) *Attorney, Agent, or Firm*—Peter Zawilski

(57) ABSTRACT

A method of examining a wafer of crystalline semiconductor material by means of X-rays, in which method a surface of the wafer is scanned by means of an X-ray beam and secondary radiation generated by said X-ray beam is detected. Prior to the examination the surface of the wafer which is to be scanned by the X-ray beam during the examination is glued to a substrate, after which crystalline semiconductor material is removed at the side which is then exposed, removal taking place as far as the top layer which adjoins the surface. The top layer can thus be examined without the examination being affected by crystal defects or impurities present in layers of the wafer which are situated underneath the top layer.

5 Claims, 1 Drawing Sheet

METHOD OF EXAMINING A WAFER OF SEMICONDUCTOR MATERIAL BY MEANS OF X-RAYS

Figure 1:
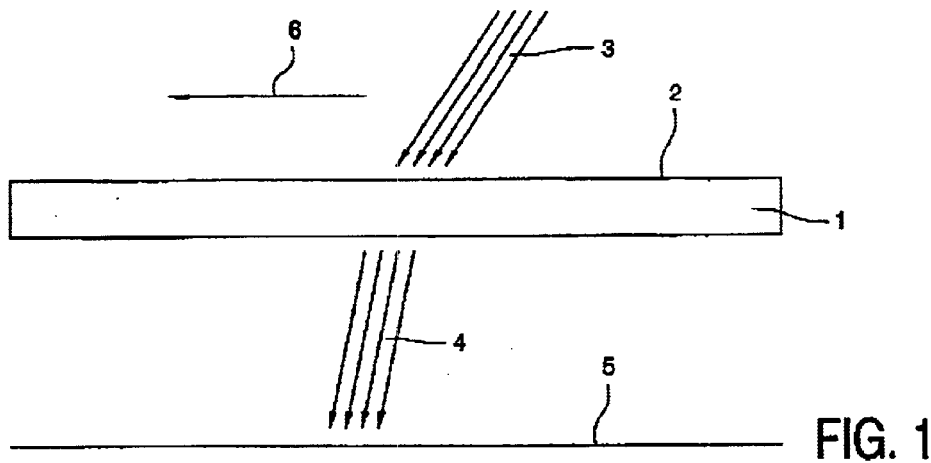

The invention relates to a method of examining a wafer of crystalline semiconductor material by means of X-rays, in which method a surface of the wafer is scanned by means of an X-ray beam and secondary radiation generated by such a beam is detected.

The secondary radiation may be caused by X-ray diffraction due to interaction of the X-ray beam with crystal faces present in the semiconductor body. In order to generate secondary radiation by X-ray diffraction, the slice is scanned at such an angle and by means of an X-ray beam of a wavelength such that Bragg's condition is satisfied. A comparatively strong beam of secondary X-rays can then be detected at the rear of the wafer. In practice the beam emanating from the rear of the wafer is recorded on a photographic plate. An image is formed on the photographic plate during the scanning of the surface of the wafer. If the wafer does not contain crystal defects, the emanating beam will exhibit a constant intensity and a uniform optical density will be obtained for the photographic plate. However, if the wafer contains crystal defects, an image is formed which enables localization and characterization of such crystal defects in the wafer. This technique is also referred to as X-ray topography.

During the formation of semiconductor circuits in wafers of semiconductor material, mutually isolated active regions are formed in these wafers, that is, adjacent the surface thereof; in silicon wafers they are formed, for example, by local oxidation of silicon. Subsequently, doping agents are applied to such active regions, for example, by ion implantation. The wafers are then often subjected to thermal treatments at high temperatures. These processes should be executed very precisely and in extremely clean environments. During such processes errors may occur, giving rise to crystal defects while undesirable impurities are built in. Consequently, it may occur that the semiconductor circuits formed do not function properly. Such defects can be traced by means of a method of the kind set forth. In many cases the cause of such defects can also be determined, thus enabling suitable steps to be taken. Crystal defects may be caused by incorrectly executed thermal treatments or by the processing of the wafers under stress. Crystal defects may also arise during the application of doping agents by ion implantation and a subsequently executed finishing treatment at a high temperature in order to repair any damage to the crystal lattice.

It has been found in practice that the described examination is impeded by crystal defects and undesirable impurities which are not due to errors made during the formation of semiconductor elements. Such crystal defects and impurities are liable to influence the measurements to such an extent that the crystal defects and impurities which are actually of interest and are caused by errors during the formation of semiconductor elements cannot be suitably detected.

It is an object of the present invention to mitigate the described drawback. To this end, a method of the kind set forth in accordance with the invention is characterized in that, prior to the execution of the examination by means of X-rays, the surface of the wafer which is to be scanned by the X-ray beam during the examination is glued to a substrate, after which crystalline material is removed from the wafer, that is, from its free side which is thus exposed and as far as a top layer which adjoins the surface.

Thus, prior to the examination layers of semiconductor materials which are situated deeper underneath the top layer are removed. It is exactly in these deeper layers that crystal defects are deliberately introduced in practice. A practical semiconductor wafer has a thickness of, for example 600 $\mu$m and only a top layer of a thickness of from approximately 5 to 30 $\mu$m thereof is treated during the formation of semiconductor elements. In order to ensure that this top layer is as free from impurities as possible, crystal defects are deliberately introduced into said deeper layers of the wafer so as to bind said impurities. Such deeper crystal defects and bound impurities are not influenced by the formation of semiconductor elements in the top layer but are detected by means of the known method. This has an adverse effect on the localizing of possible crystal defects and contaminations in the top layer. According to the method of the invention such deeper layers of semiconductor material are removed prior to the examination, so that they can no longer influence the measurements. Surprisingly, it has been found in practice that the removal of the semiconductor material does not introduce new crystal defects and impurities to any significant extent and that a layer is obtained which has a thickness which is so uniform that the measuring results are not affected by differences in thickness. Differences in thickness could lead to undesirable diffraction patterns in the photographic image in the case of X-ray topography.

Preferably, the wafer is glued to a substrate of a material which transmits X-rays. Suitable materials for the substrate are inter alia lead-free glasses, quartz glass and aluminum oxide. Use is preferably made of a substrate of boron nitride, because such a substrate is practically completely transparent to X-rays; a substrate having a thickness of, for example, 500 $\mu$m transmits 95% of the radiation.

Preferably, the material of the wafer is removed as far as the top layer in two steps, removal taking place almost to the vicinity of the top layer in a first step by means of a chemical-mechanical polishing treatment, after which the top layer is exposed in the second step by means of an etching treatment during which crystal defects caused by the polishing treatment are removed by etching. Thus, the material is removed comparatively quickly by way of the polishing treatment and any crystal defects caused by the polishing treatment are removed by the etching treatment. Moreover, these steps yield a layer of very uniform thickness which is attached to the substrate.

During the examination of a wafer of semiconductor material with a top layer of crystalline semiconductor material which is situated on a layer of insulating material and adjoins the surface, the semiconductor material of the wafer is removed to such an extent that the layer of insulating material is exposed. In order to examine such an SOI wafer by means of X-rays, it is advantageous to stop the removal of semiconductor material at the layer of insulating material; this layer can be used as a layer on which the etching treatment stops automatically.

Figure 2:
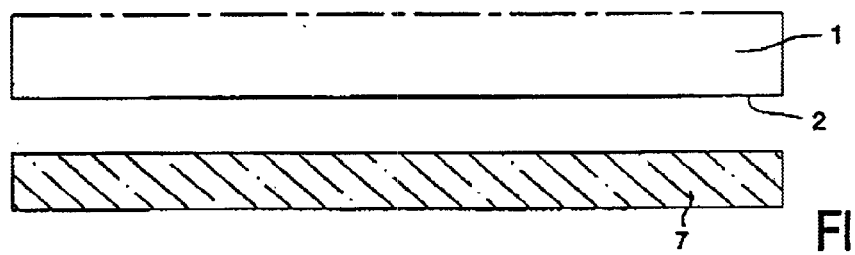
Figure 3:
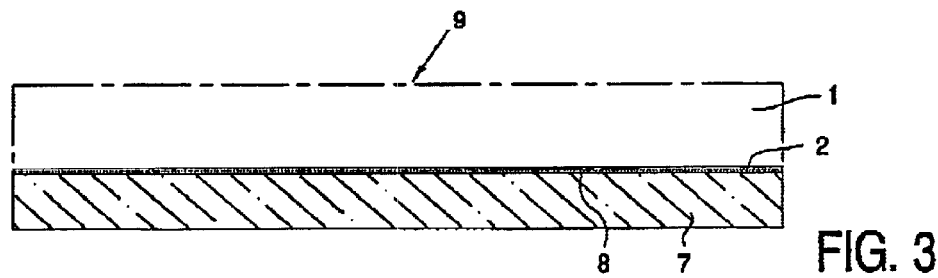
Figure 4:
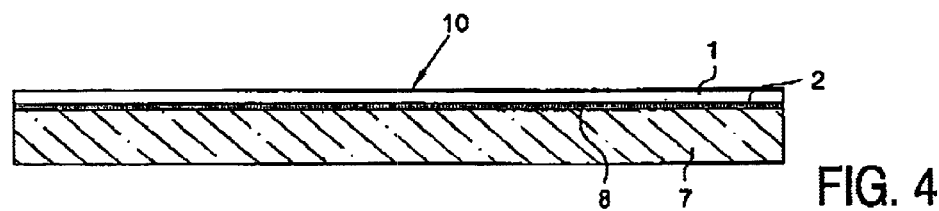

The invention will be described in detail hereinafter, by way of example, with reference to a drawing. Therein:

FIG. 1 shows diagrammatically an arrangement for the examination of a semiconductor wafer by means of X-ray topography, and FIGS. 2 to 4 are diagrammatic sectional views elucidating some steps for preparing a wafer of semiconductor material for the examination in accordance with the invention.

FIG. 1 shows diagrammatically an arrangement for examining a wafer of crystalline semiconductor material 1 by means of X-rays, in this case being a customary wafer of silicon. It will be evident that wafers of another crystalline semiconductor material can also be examined in this manner. A surface 2 of the wafer 1 is scanned by means of an X-ray beam 3, in this case being a beam having a dimension of a few millimeters in the plane of drawing and dimensions in the direction perpendicular to the plane of drawing which are such that the entire diameter of the wafer 1 is irradiated. The X-ray beam 3 is incident on crystal faces in the semiconductor body, which faces do not necessarily extend parallel to the surface 2; the beam is incident at such an angle and contains radiation of such a wavelength that Bragg's condition is satisfied. In that case X-ray diffraction occurs, so that a comparatively strong beam of secondary X-rays 4 emanates at the rear of the wafer 1, that is, at an angle which is defined by Bragg's condition. The beam 4 generated by X-ray diffraction is detected. In this case this is realized by recording the beam 4 on a photographic plate 5. During the examination the surface 2 of the wafer 1 is scanned in a direction as denoted by the arrow 6. During the scanning of the surface of the wafer, an image is formed on the photographic plate. If the wafer does not contain crystal defects, the emanating beam will exhibit a constant intensity and a uniform optical density is obtained on the photographic plate. However, if the wafer contains crystal defects, an image is formed such that it is suitable for localizing and characterizing such crystal defects in the wafer. This technique is also referred to as X-ray topography.

The FIGS. 2 to 4 are diagrammatic cross-sectional illustrations of some steps for preparing a silicon semiconductor wafer for one of the above examinations. The surface 2 of the wafer 1 which is to be scanned by means of the X-ray beam during the examination is glued to a substrate 7. In the present example the wafer is glued to a substrate 7, consisting of a plate of quartz glass, by means of a layer of epoxy or acrylate glue 8. Subsequently, crystalline material is removed from the wafer 1, that is, from its exposed side 9 and as far as a top layer 10 which adjoins the surface. The structure 7, 8, 10 thus formed is subsequently examined by means of X-rays.

Prior to the execution of the examination by means of X-rays, therefore, layers of semiconductor material which are situated deeper underneath the top layer 10 are removed. In practice crystal defects are introduced deliberately in particular in such deeper layers. A semiconductor wafer in practice has a thickness of, for example 600 $\mu$m and during the formation of semiconductor elements in the wafer only a top layer 10 thereof, having a thickness of only from approximately 5 to 30 $\mu$m, is treated. In order to ensure that this top layer 10 is as free from impurities as possible, crystal defects are deliberately introduced in said deeper layers of the wafer in order to bind such impurities. Because the deeper layers are removed, such crystal defects and impurities cannot affect the measurements. Crystal defects and impurities in the top layer can thus be suitably localized and characterized.

The removal of the semiconductor material introduces practically no new crystal defects and impurities and, moreover, a layer is obtained which has a thickness which is so uniform that the measuring results are not influenced by differences in thickness which could lead to undesirable diffraction patterns in the photographic image in the case of X-ray topography.

The wafer 1 is glued to a substrate 7 which is transparent to X-rays. Inter alia lead-free glasses, quartz glass and aluminum oxide are suitable materials for the substrate. Preferably, use is made of a substrate of boron nitride, because such a substrate is practically completely transparent to X-rays; a substrate of a thickness of, for example, 500 $\mu$m transmits 95% of molybdenum k$\alpha$1 radiation.

In the present example the semiconductor material of the wafer 1 is removed as far as the top layer 10 in two steps. During a first step the material is removed as far as the vicinity of the top layer of approximately 50 $\mu$m by means of a conventional chemical-mechanical polishing treatment, after which in the second step the top layer 10 is exposed by means of an etching treatment in a conventional etching bath with hydrogen fluoride and nitric acid. Crystal defects caused by the polishing treatment are removed by etching during the etching treatment. The material is thus comparatively quickly removed by means of the polishing treatment and any crystal defects introduced by the polishing treatment are removed by the etching treatment. Moreover, a top layer 10 to be examined, attached to the substrate 7, thus has a very uniform thickness.

For the examination of a wafer of semiconductor material (not shown) with a top layer of crystalline semiconductor material which is situated on a layer of insulating material and adjoins the surface, the semiconductor material of the wafer is removed to such an extent that the layer of insulating material is exposed. In order to examine such an SOI wafer by means of X-rays, it is advantageous to make the removal of semiconductor material stop at the layer of insulating material; this layer can then be used as a layer on which the etching treatment stops automatically.

What is claimed is:

1. A method of examining a wafer of crystalline semiconductor material by means of X-rays, in which method a surface of the wafer is scanned by means of an X-ray beam and secondary radiation generated by such a beam is detected, characterized in that, prior to the examination by means of X-rays, the surface of the wafer which is to be scanned by means of the X-ray beam during the examination is glued to a substrate, after which crystalline material is removed from the wafer, that is, from its free side which is thus exposed and as far as a top layer which adjoins the surface.

2. A method as claimed in claim 1, characterized in that the wafer is glued to a substrate of a material which is transparent to X-rays.

3. A method as claimed in claim 2, characterized in that the wafer is glued to a substrate of boron nitride.

4. A method as claimed in claim 1, characterized in that material of the wafer is removed as far as the top layer in two steps, removal taking place as far as the vicinity of the top layer in a first step by means of a chemical-mechanical polishing treatment, after which the top layer is exposed in the second step by means of an etching treatment during which crystal defects caused by the polishing treatment are removed by etching.

5. A method as claimed in claim 1, characterized in that during the examination of a wafer of semiconductor material with a top layer of crystalline semiconductor material which is situated on a layer of insulating material and adjoins the surface the semiconductor material of the wafer, the semiconductor material is removed so far that the layer of insulating material is exposed.

* * * * *